United States Patent [19]

Harding, Jr.

[11] Patent Number: 4,756,755
[45] Date of Patent: * Jul. 12, 1988

[54] RODENT REPELLENT LIQUIDS

[76] Inventor: Norman T. Harding, Jr., 2320 Laketon Rd., Pittsburgh, Pa. 15221

[*] Notice: The portion of the term of this patent subsequent to May 26, 2004 has been disclaimed.

[21] Appl. No.: 52,078

[22] Filed: May 21, 1987

Related U.S. Application Data

[63] Continuation-in-part of Ser. No. 913,363, Sep. 30, 1986, Pat. No. 4,668,294, which is a continuation-in-part of Ser. No. 745,356, Jun. 14, 1985, Pat. No. 4,654,080.

[51] Int. Cl.$^4$ ................................................ C09D 5/14
[52] U.S. Cl. ................................ 106/15.05; 424/195.1
[58] Field of Search ................... 106/15.05; 424/195.1

[56] References Cited

U.S. PATENT DOCUMENTS

| | | |
|---|---|---|
| 1,771,461 | 7/1930 | Lilienfeld . |
| 2,129,708 | 9/1938 | Schreiber . |
| 2,134,825 | 11/1938 | Hill et al. ............................ 260/10 |
| 3,454,982 | 7/1969 | Arnold ................................. 17/42 |
| 3,456,286 | 7/1969 | Martinek .............................. 17/49 |
| 3,940,488 | 2/1976 | Frohberger ......................... 514/920 |
| 4,390,490 | 6/1983 | Martinek et al. ................... 264/173 |
| 4,404,369 | 9/1983 | Huttunen et al. .................... 536/30 |
| 4,526,620 | 7/1985 | Selin et al. ......................... 106/203 |
| 4,530,999 | 7/1985 | Selin et al. .......................... 536/30 |
| 4,654,080 | 3/1987 | Harding ........................... 106/15.05 |
| 4,668,294 | 5/1987 | Harding ........................... 106/15.05 |

FOREIGN PATENT DOCUMENTS 0178292 4/1986 European Pat. Off. .

*Primary Examiner*—Theodore Morris
*Attorney, Agent, or Firm*—Buchanan Ingersoll

[57] ABSTRACT

Rodent repellent liquids are disclosed which are comprised of thujone oil in pure form or in the form of cedar leaf oil in a suitable low odor liquid carrier such as mineral oil.

4 Claims, No Drawings

RODENT REPELLENT LIQUIDS

CROSS REFERENCE TO RELATED APPLICATION

This application is a continuation-in-part of my copending application Ser. No. 913,363, filed Sept. 30, 1986, now U.S. Pat. No. 4,668,294 which is a continuation-in-part of Ser. No. 06/745,356, filed June 14, 1985, now U.S. Pat. No. 4,654,080.

FIELD OF INVENTION

The present invention relates to a liquid having rodent repellent characteristics.

DESCRIPTION OF THE PRIOR ART

For many years numerous attempts have been made to keep rats and mice away from homes, storage bins and other areas. Most commonly, traps or poisons are used to kill the vermin. In addition to creating dead animal disposal problems, traps and poisons also pose dangers to children, pets and animals. Furthermore, traps and poisons must be monitored. Sprung traps must be reset and consumed poison must be replaced. Also, many people have found that for each rat they kill with traps or poison there are others in the area who survive.

Rather than try to kill the rodents which are present, a better approach is to deter them from entering the area. Certain plant extracts have been found to have repellent properties Bottrell in U.S. Pat. No. 1,871,949 uses oil of peppermint to repel rodents. Cross in U.S. Pat. No. 2,159,550 teaches that extracts from the wood and fruit of the Areca catechu plant have repellent properties. Yet, neither of these materials have had any commercial success.

The art has also recognized that certain plants repel rodents. For example, pieces of the wormwood plant (*Artemsia Absinthium*) have been used as moth and rodent repellents. But, these pieces are only effective for a relatively short period of time, typically a few days.

The art has generally attributed the repellent characteristics of the wormwood and other plants to the presence of alkyloids in the plant. Apparently, these alkyloids are poisonous. However, I have discovered that thujone oil, a natural oil of the wormwood plant and a component of cedar leaf oil from the cedar tree, not alkyloids, will repel rodents when used in the manner here described.

In my U.S. Pat. Nos. 4,668,294 and 4,654,080 I disclose liquid rodent repellents in which thujone oil is combined with sodium silicate, lacquer or kerosene. Although these products work well they are not suitable for warm environments. The flash points of lacquer and kerosene are so low that there is a risk of ignition. Thus, there is a need for a liquid rodent repellent which is non-flammable.

SUMMARY OF THE INVENTION

I provide a rodent repellent in liquid form by combining pure thujone oil or cedar leaf oil which contains thujone oil with a low odor liquid carrier. Several liquids such as mineral oil, alcohol, kerosene or lacquer are suitable.

I prefer to use a liquid comprised of thujone oil in the form of cedar leaf oil and a low odor liquid carrier, such as mineral oil, in a mixture having from 0.5 to 10 ounces carrier per 1 ounce cedar leaf oil. If pure thujone oil is used the mixture should contain a higher percentage of carrier.

DESCRIPTION OF THE PREFERRED EMBODIMENTS

I have found that certain compositions of thujone oil or cedar leaf oil and a low odor liquid carrier will repel rodents for a significant period of time. A combination of thujone oil or cedar leaf oil and liquid when used like a paint will keep rodents away from the painted area for between three and five years.

To make these products, I first extract the oil from the plant source. Thujone oil is extracted from the wormwood plant and cedar leaf oil is obtained from the cedar tree. Thujone oil is also commercially available as it is used in perfume. Both oils have a similar aroma and can be used interchangeably. Then the oil is combined with a suitable, low odor carrier such as mineral oil, alcohol, white kerosene or any of the low odor solvents sold by Exxon under the trade name ISOPAR.

I have found that mineral oil is a suitable carrier for thujone oil and cedar leaf oil. Cedar leaf oil and mineral oil are combined to provide from 0.5 to 10 ounces mineral oil per ounce of cedar leaf oil. Then, the combination is applied to a surface like any standard paint.

Other low odor carriers in addition to mineral oil could also be used as a carrier. These solvents must be non-reactive with thujone oil and evaporate at room temperature or lower. They also must not leave an odorous residue which would overpower the odor of thujone oil.

I have conducted several experiments to show the effectiveness of my rat and mice repellents. The first experiment consisted of three boxes with the entrances to each blocked with sheets of screen. The rats were placed in the middle box. The box on the left contained food and the walls of the box were stained with the rat and mice repellent. This repellent was a mixture of 12% thujone oil and 88% lacquer. The box on the right contained only food and the walls were not stained. At the end of five days, the metal screens were lifted. The rats would not enter the box with the rat and mice repellent, but ate from the box that contained no repellent.

I have also applied my liquid repellent to underfloor areas of homes that I identified as rodent nests or pathways. A few days later I returned and saw no signs of rats or mice. The owners of the homes I treated also reported no signs of rodents after treatment.

In a second experiment, I used two boxes separated by a metal screen. A neutral box without repellent on the walls housed the rats. The remaining box contained the rat and mice repellent and contained the food. After five days the metal screen which separated the boxes was lifted. The rats would not enter the box stained with the rat and mice repellent to get the food. The repellent used in this experiment was a mixture of 12% thujone oil and 88% lacquer.

While I have described certain present preferred embodiments of my invention, it should be distinctly understood that the invention is not limited thereto but may be variously embodied within the scope of the following claims.

I claim:

1. A rodent repellent liquid comprised of thujone oil and a low odor liquid carrier, said carrier being non-reactive with thujone oil producing a residue having an odor which does not overpower the thujone oil's odor.

2. The rodent repellent liquid of claim 1 wherein at least a portion of the thujone oil is in the form of cedar leaf oil.

3. A rodent repellent liquid of claim 1 comprised of from 0.5 to 10 ounces of liquid carrier per ounce of cedar leaf oil.

4. The rodent repellent liquid of claim 1 wherein the liquid carrier is selected from the group of carriers comprised of mineral oil, vegetable oil and isoparaffinic solvents.

* * * * *